United States Patent [19]

Carlo et al.

[11] 4,203,970

[45] May 20, 1980

[54] SWINE ATROPIC RHINITIS VACCINE

[75] Inventors: Dennis J. Carlo, Rahway; Arpi Hagopian; Peter J. Kniskern, both of Sayreville, all of N.J.

[73] Assignee: Merck & Co., Inc., Rahway, N.J.

[21] Appl. No.: 17,528

[22] Filed: Mar. 5, 1979

[51] Int. Cl.$^2$ .............................................. A61K 39/02
[52] U.S. Cl. ....................................................... 424/92
[58] Field of Search ............................................ 424/92

[56] References Cited

PUBLICATIONS

Harris et al., Am. J. Vet. Res. 33(10):1975–1984 (1972) Immunization of Pigs against *Bordetella bronchiseptica* Infection by Parenteral Vaccination.
Goodnow Vet. Med. & Small Anim. Clin. 72(7):1210–1212 (1977) Control of Atrophic Rhinitis with a *Bordetella bronchiseptica* Bacterin.
Brandenburg Can. J. Comp. Med. 42(1):23–28 (1978) Bordetella Rhinitis in Pigs: Serum and Nasal Antibody Response to Bordetella Bacterins.
Goodnow et al. Am. J. Vet. Res. 40(1):58–60 (1979) Efficacy of *Bordetella bronchiseptica* Bacterin in Controlling Enzootic Atrophic Rhinitis in Swine.

*Primary Examiner*—Shep K. Rose
*Attorney, Agent, or Firm*—Donald J. Perrella; Julian S. Levitt; Theresa Y. Cheng

[57] ABSTRACT

A sub-cellular antigenic fraction of *Bordetella bronchiseptica* protects against the incidence and severity of swine atropic rhinitis.

5 Claims, No Drawings

SWINE ATROPIC RHINITIS VACCINE

BACKGROUND OF THE INVENTION

Atropic rhinitis is prevalent in various countries of the world and causes severe economic losses in the swine-raising industry in terms of both inhibition of growth and reduction of feed efficiency. The causative agent for this disease has been shown to be *B. bronchiseptica*. At least 1.8 million cases occur in the U.S. alone each year and entire herds may become infected before clinical signs appear. Once apparent, the effect in terms of morbitity is essentially irreversible despite the use of antibiotics. Therefore, prophylaxis rather than cure is the only way to control this disease.

OBJECTS OF THE INVENTION

It is an object of the present invention to provide a safe and effective vaccine to prevent atrophic rhinitis. Another object is to provide a sub-cellular vaccine to eliminate the incedence and severity of atrophic rhinitis in swine. A further object is to provide a biochemically characterized sub-cellular vaccine which protects swine against atropic rhinitis. Still another object is to provide formulations for administering this vaccine. Another object is to provide a method for preparing this vaccine. Yet another object is to provide methods of administering this vaccine. These and other objects of the present invention will be apparent from the following description.

SUMMARY OF THE INVENTION

A sub-cellular vaccine effective against atropic rhinitis isolated from a cell wall antigenic fraction of a pathogenic isolate of *B. bronchiseptica* chemically characterized in containing from about 53 to about 57% protein (Lowry), from about 10 to 13% carbohydrate (of which about 19% is hexose and about 19% hexosamine), from about 1 to about 1.4% sialic acid, and about 0.18% 2-keto-3-deoxyoctanate (KDO).

DETAILED DESCRIPTION

The present invention relates to the isolation and purification of a cell wall fraction of a pathogenic isolate of *B. bronchiseptica*. The cell wall fraction is obtained from a killed cell paste of *B. bronchiseptica*. The cells may be killed by suitable means, e.g., chemical treatment. The killed cell paste is homogenized, e.g., by high speed mixing, extracted in an aqueous medium and centrifuged. The homogenization takes place in the presence of a salt of a strong acid and a strong base, e.g., LiCl, at a concentration of from about 0.05 M to about 1 M, or in the presence of a nonionic detergent such as alkyl phenoxy polyethoxy ethanol (Triton X-100) or an anionic detergent such as sodium deoxycholate. The detergent is employed at a concentration of from about 0.5 to about 10%. The treatment with the salt or detergent disrupts ionic bonds and salt bridges which maintain the integrity of the bacterial membrane and cell wall. Treatment with salt is preferred. A product of enhanced purity is obtained, although in reduced yield, by a combined treatment using salt and detergent sequentially. The extraction may take place at room temperature or at lowered temperatures down to about 4° C. or at elevated temperatures up to about 75° C. In general extraction times are reduced at elevated temperatures. The centrifugation takes place at from about 12,000 XG to about 20,000 XG for from about 0.5 hour to about 3 hours. In general centrifugation time at higher G force is reduced. The supernatant fluid resulting from the centrifugation is treated with RNase and DNase under conditions effective to digest nucleic acids, and dialyzed to remove nucleic acid fragments and to yield the desired antigenic fraction. The dialyzed antigen may be lyophilized for storage. Alternatively the dialysed product may be subjected to column chromatography, e.g., Sepharose 4B, Biogel 1.5 M or 5 M, and the like, whereby the first peak is collected and used as the desired antigenic fraction.

The cell wall antigenic fraction of the present invention is immunogenic and protects both mice and swine against both homologous and heterologous challenge with a pathogenic isolate of *B. bronchiseptica* field isolates. The sub-cellular cell wall antigenic fraction of a pathogenic isolate of *B. bronchiseptica* obtained according to the foregoing method is chemically characterized in containing at least about 53% Lowry protein, typically from about 53 to about 57% Lowry protein, from about 10 to about 13% carbohydrate (of which about 19% is hexose, and about 19% is hexosamine), from about 1 to about 1.4% sialic acid, and about 0.18% KDO.

The cell wall antigenic fraction of the present invention may be sterilized by filtration or treatment by chemicals such as thimerosol, phenol, formaldehyde and the like, and subdivided into a suitable container for distribution and administration as a vaccine. It may be administered in a suitable physiologically acceptable medium such as, for example, water for injection, saline, phosphate buffered saline, and the like. It may be combined with adjuvants such as, for example, those disclosed in U.S. Pat. No. 3,983,228 or with carriers, e.g., alum.

The following examples illustrate the present invention without, however, limiting the same thereto.

EXAMPLE 1

A cell paste of *B. bronchiseptica* killed with thimerosal and harvested by Sharples centrifugation is fractionated to obtain and characterize protective vaccine cell wall fractions. Initially, the wet cell paste is homogenized with 0.2 M LiCl in an electric blender with overhead blades at a concentration of 20 ml/gram of wet paste. This mixture is then extracted in a shaking water bath for 2 hours at 45° C., and subsequently centrifuged at 16,000×G for 60 minutes at 20° C. The supernatant fluid is made 1.0 mM in $MgCl_2$, brought to 37° C. and digested for 45 minutes with pancreatic RNAse and DNAse at concentrations of 10 μg/ml each. The mixture is then dialyzed against $H_2O$ and lyophilized. All fractions are tested for protective activity as explained below. Both the extract and the residue are active; a second extraction of the cell paste, however, removes the residual activity. The lyophilized extract is chromatographed on a BioGel 5 M column and fractionated into numerous sub-fractions; however, only one of these (eluting at 1 $V_o$) is protective. This material although substantially enriched in protective immunogen is neither immunologically nor chemically homogeneous. It is characterized chemically as having the following analysis:

| Assay | | |
|---|---|---|
| Protein | Lowry | 54.4% |

-continued

| Assay | | |
|---|---|---|
| Hexoses | Anthrone | 2.45 |
| Carbohydrate | Phenol-$H_2SO_4$ | 11.5 |
| | | 1.6 |
| Hexosamine | Berman-Gatt | 2.5 |
| Sialic Acid | Warren | 1.2 |
| KDO | Osborn | 0.18 |

This fraction protects mice, at dosed of 1–100 μg, not only against homologous challenge, but also against challenge with heterologous *B. bronchiseptica* isolates.

EXAMPLE 2

Fourteen groups of mice (10 animals per group) are injected intraperitoneally (I.P.) with 0.1 ml of a PBS (phosphate buffered saline) solution containing 100 μg of the product of Example 1 or with 0.1 ml of PBS only. Seven to fourteen days post immunization, the mice are challenged with varying amounts of differing strains of *B. bronchiseptica* (I.P. injection in 1.0 ml 7.5% Hog Gastric Mucin/mouse). The mice are observed daily and the percentage of survivors determined after 3 days. The following results are obtained:

| Group | Challenge Strain | No. of Bacteria | % Survivors No Antigen | % Survivors 100 μg Antigen |
|---|---|---|---|---|
| I | Homologous | $10^4$ | 10 | 90 |
| II | Homologous | $10^6$ | 0 | 80 |
| III | MO-2 | $10^3$ | 100 | 100 |
| IV | MO-2 | $10^4$ | 100 | 100 |
| V | MO-2 | $10^5$ | 30 | 100 |
| VI | MO-2 | $10^6$ | 0 | 100 |
| VII | SD12972 | $10^3$ | 100 | 100 |
| VIII | SD12972 | $10^4$ | 80 | 100 |
| IX | SD12972 | $10^5$ | 80 | 100 |
| X | SD12972 | $10^6$ | 10 | 100 |
| XI | ILL4673 | $10^3$ | 100 | 100 |
| XII | ILL4673 | $10^4$ | 90 | 100 |
| XIII | ILL4673 | $10^5$ | 55 | 100 |
| XIV | ILL4673 | $10^6$ | 10 | 90 |

EXAMPLE 3

Four groups of pigs (16 animals per group) infected with *B. bronchiseptica* and one group of 16 uninfected pigs are injected as indicated in the following table.

| Group | Material Injected | Rhinitis Score |
|---|---|---|
| 1 (Uninfected) | PBS, no antigen (control) | 2.69 |
| 2 (Infected) | Product of Example 1, PBS and Adjuvet | 1.94 |
| 3 (Infected) | Product of Example 1, Adjuvet (2X) | 2.50 |
| 4 (Infected) | Product of Example 1, Burns-Biotec (2X), PBS | 5.19 |
| 5 (Infected) | PBS, no antigen (control) | 8.53 |

EXAMPLE 4

The procedure of Example 3 is repeated with another four groups of pigs (16 animals per group ) infected with *B. bronchiseptica* and one group of 16 uninfected pigs are injected as indicated in the following table.

| Group | Material Injected | Rhinitis Score |
|---|---|---|
| 1 (Uninfected) | PBS, no antigen (control) | 3.46 |
| 2 (Infected) | Product of Example 1, PBS and Adjuvet | 3.08 |
| 3 (Infected) | Product of Example 1, PBS (2X) | 4.93 |
| 4 (Infected) | Product of Example 1, Alum (2X) | 4.86 |
| 5 (Infected) | PBS, no antigen (control) | 8.31 |

EXAMPLE 5

A portion of the final product of Example 1 (10 mg) is added with stirring to 2 ml of water, and 1 ml of a 25% suspension of a mixture of $Al_2O_3$ and $Al(OH_3)$ (alum), and 5 ml of water. Over 90% of the Lowry protein is adsorbed to the alum.

EXAMPLE 6

A portion of the final product of Example 1 (25 mg) is added to 10 ml of PBS. While stirring 0.1 N NaOH is added slowly to adjust the pH to 6.8. Mixing is continued for 1 hour at room temperature. The solution is then centrifuged at 1,500×G for 10 minutes. The supernatant liquid is decanted and the pellet is resuspended with saline solution to the original volume (10 ml).

EXAMPLE 7

A portion of the final product of Example 1 (25 mg) is added to a mixture of 5 ml of a peanut oil adjuvant prepared as described in Example 5 of U.S. Pat. No. 4,069,313 and 5 ml of PBS with agitation until a uniform mixture is obtained.

EXAMPLE 8

The procedure of Example 1 is repeated except that the cell paste is extracted with 2% Triton X-100 for 30 minutes at room temperature rather than with LiCl. The yield is 35% of that obtained with LiCl and on an equal weight basis the antigenic product is only about 20% as effective as that obtained with LiCl.

EXAMPLE 9

The final product of Example 1 is further purified by extraction with 5% Triton X-100 for one hour at room temperature. This treatment removes most of the endotoxin contaminant although the protective antigen is recovered only in about 10% yield.

EXAMPLE 10

A cell paste prepared as described in Example 1 is homogenized by pressure (15,000 psi, 1,020 atmospheres). The cell walls are separated from cytoplasmic fluid and unbroken cells by differential centrifugation. The cell walls are washed with and extracted with sodium deoxycholate (1%). The extract is separated from the cell wall residue, precipitated sequentially with 50% ammonium sulfate and 80% ethanol, dialyzed and lyophilized. The lyophilized product is as protective to mice against a lethal dose of *B. bronchiseptica* as the LiCl extracted product but purer as it contains a higher percentage of protein and less lipopolysaccharide. The yield, however, is very low (about 5%) compared to the use of LiCl.

EXAMPLE 11

The final product of Example 1 is further fractionated on Sephadex G-100 columns to remove the lipopolysaccharides. The gel filtration on Sephadex G-100 is carried out in the presence of 0.5% sodium deoxycholate, 1 mM ethylenediaminetetraacetic acid, and 0.05 glycine, pH 10. In preparation for chromatography, the samples are resuspended in 10 mg/ml in the above buffer, except that the sodium deoxycholate concentration is 1% and the pH is 11.5. These suspensions are centrifuged at $100,000 \times G$ for 2 hours and the clear supernatant fluids are applied to G-100 columns. The column fractions are monitored for refractive index and optical density at 260 and 280 m$\mu$; fractions are also assayed for KDO and carbohydrate (phenol-sulfuric acid assay). The clearly resolved peaks are pooled, made 0.5 M in NaCl and 80% in ethanol. The resulting precipitates are collected by centrifugation, washed with ethanol and acetone and dried over $CaCl_2$ in vacuo at 4° C. The individual peaks are chemically characterized. The Vo peak of G-100 column is found to be protective against a lethal dose of *B. bronchiseptica* in the hog gastric mucin mouse model.

What is claimed is:

1. An immunogenic sub-cellular cell wall antigenic fraction of *Bordetalla bronchiseptica* contains in part by weight at least about 53% Lowry protein, from about 10 to about 13% carbohydrate, of which about 19% is hexose and about 19% is hexosamine, from about 1 to about 1.4% sialic acid, and about 0.18% KDO.

2. A composition according to claim 1 containing from about 53% to about 57% Lowry protein.

3. A composition comprising the antigenic fraction of claim 1 and a physiologically acceptable medium.

4. A composition comprising the antigenic fraction of claim 1 and a physiologically acceptable vaccine adjuvant.

5. A composition comprising the antigenic fraction of claim 1 and a carrier.